US008147878B2

(12) United States Patent
Bonanomi et al.

(10) Patent No.: US 8,147,878 B2
(45) Date of Patent: Apr. 3, 2012

(54) WATER INSOLUBLE HELYCHRISUM EXTRACT, PROCESS FOR PREPARING THE SAME AND USES THEREOF

(75) Inventors: Michele Bonanomi, Rome (IT); Bruno Silvestrini, Rome (IT); Caterina Ghiara, Sansepolcro (IT); Valentino Mercati, Sansepolcro (IT)

(73) Assignee: Aboca S.p.A. Societa' Agricola, Sansepocro (IT)

( * ) Notice: Subject to any disclaimer, the term of this patent is extended or adjusted under 35 U.S.C. 154(b) by 373 days.

(21) Appl. No.: 12/160,368

(22) PCT Filed: Jan. 12, 2007

(86) PCT No.: PCT/IB2006/003921
§ 371 (c)(1),
(2), (4) Date: Jul. 9, 2008

(87) PCT Pub. No.: WO2007/083190
PCT Pub. Date: Jul. 26, 2007

(65) Prior Publication Data
US 2011/0250301 A9    Oct. 13, 2011

(30) Foreign Application Priority Data
Jan. 17, 2006   (IT) .............................. MI2006A0063

(51) Int. Cl.
*A01N 65/00*    (2009.01)

(52) U.S. Cl. ....................................................... 424/725
(58) Field of Classification Search ........................ None
See application file for complete search history.

(56) References Cited

U.S. PATENT DOCUMENTS
5,785,972 A    7/1998 Tyler
2004/0258783 A1   12/2004 Millou
2005/0003028 A1   1/2005 Leko FOREIGN PATENT DOCUMENTS
| FR | 2774585 | 8/1999 |
| FR | 2830198 | 4/2003 |
| FR | 2845594 | 4/2004 |
| KR | 2003046949 | 6/2003 |
| WO | WO0207744 A1 | 1/2002 |
| WO | WO03015522 A1 | 2/2003 |
| WO | WO03046949 | 5/2003 |

OTHER PUBLICATIONS

Guida et al., Boll. Chim. Farmaceutico—Anno 138, No. 7, 1999, pp. 369-373.*
Cubukcu B. et al., "A Further Investigation on the Flavonoids of Helichrysum-Orientale", 1981, Journal of the Faculty of Pharmacy of Istanbul University, Istanbul, TR, pp. 86-90.
Database WPI Week 200340, Derwent Publications Ltd., London, GB; AN 2003-422206, XP002437982 & CN 1 395 941 A (Yin D), Feb. 12, 2003, Abstract.
Hutchings Anne, et al., "Plants Used for Stress-Related Ailments in Traditional Zulu, Xhosa and Sotho Medicine, Part 1: Plants Used for Headaches", Journal of Ethnopharmacology, vol. 43, No. 2, 1994, pp. 89-124.
Facino R M, et al., "Anti-Erythematous and Photoprotective Activities in Guinea-Pigs and in Man of Topically Applied Flavonoids From Helichrysum-Italicum G. Don", 1988, Acta Therapeutica, vol. 14, No. 4, pp. 323-346.
"Erythema"; Wikipedia; Wikimedia Foundation, Inc.; Feb. 3, 2009, p. 1 of 1. An erythem is a skin redness due to inflammation.
Jager, Anne K., et al., "Screening of Zulu Medicianl Plants for Prostaglandin-Synthesis Inhibitors", Journal of Ethnopharmacology, Published by Elsevier Science Ireland, Ltd, Ireland; vol. 52, 1996, pp. 95-100.
Cubukcu, Bayhan, "Helichrysum Species as Choleretic and Chologogue Crude Drugs", Acta Pharmaceutica Turcica, Published by Istanbul University, Turkey; vol. 44; 2002, pp. 145-150.
Sala, Ariceli, et al., "Anti-Inflammatory and Antioxidant Properties of Helichrysum Italicum", Journal of Pharmacy and Pharmacology, vol. 54, 2002, pp. 365-371.

* cited by examiner

*Primary Examiner* — Michael Meller
(74) *Attorney, Agent, or Firm* — Pearne & Gordon LLP (57) ABSTRACT

The present invention relates to a water insoluble helychrisum extract, a process for preparing the same and its use for preparing pharmaceutical compositions for oral and/or topical administration. Furthermore, the present invention relates to the pharmaceutical compositions including said extract.

16 Claims, 3 Drawing Sheets

WATER INSOLUBLE HELYCHRISUM EXTRACT, PROCESS FOR PREPARING THE SAME AND USES THEREOF

FIELD OF THE INVENTION

The object of the present invention is a water insoluble helychrisum extract, a process for producing the same and the use thereof for preparing pharmaceutical compositions for oral and/or topical administration. Furthermore; the present invention relates to the pharmaceutical compositions including said extract.

BACKGROUND OF THE INVENTION

Helychrisum (*Helichrysum italicum* G. Don) is a perennial plant belonging to the genus of the Asters, better known as Composites. It is an aromatic plant originating from the Mediterranean region, where it grows on dry sandy soils; its flowers are combined in corymbs and have a typical golden yellow colour, from which the name of the plant comes from (from the Greek Helios chrysos, golden sun).

The "dry drug" of the helychrisum (hereinafter, "the drug") consists of the dried flowered tops of the plant. By the term "flowered tops of the plant" is understood to mean the flowers plus the tender, non woody tops, of the branchlets, cut at about 5-15 cm from the top, preferably at about 10 cm, depending on the plant.

Amongst the chemical compounds found in the drug, there have to be mentioned the flavonoids, such as, for example: pinocembrin, apigenin, isoquercitrin, naringenin, luteolin, 7-glucoside, gnaphaline; tiliroside; 4,2',4',6'-tetrahyroxychalcone-2'-O-glucoside; naringin-4'-O-glucoside; kampferol-3-O-glucoside. Other types of chemical compounds found in the tops and the flowers of helychrisum are: phthalides (5-methoxy-7-hydroxy-phthalyde and 5,7-dimethoxyphthalide); triterpenes (ursolic acid, uvaol, α-amirine); acetophenone derivatives; caffeil-quinic derivatives; β-sitosterol; nerols and neril acetate (these latter comprise the 30-500 of the essential oils existing within the plant in a varying percentage, between 0.05% and 0.20% by weight, based on the weight of the drug, depending on the species and the season).

The essential oils are generally obtained by steam distillation of the flowered tops of the plant.

The known patent art mainly describes the use of helychrisum essential oils.

In the US 2005/0003028 patent, the use both of a decoction of a drug mixture, containing the 2% of helychrisum flowers, and an alcoholic extract of a 3:1 mixture of Marian thistle and helychrisum flowers; in both cases, the addition of helychrisum to the preparation is motivated for the detoxifying properties and assistance for the bile secretion. In the US 2004/0258783 patent application, the anti-wrinkle action exerted by the essential oil extracted by steam distillation from the flowered tops is claimed.

In the U.S. Pat. No. 5,785,972 patent, a composition containing commercial helychrisum oil (together with honey, colloidal silver, water soluble lecithin), to be used in the treatment of burns and sores is claimed.

In the WO 02/07744 patent application, an association of at least two essential oils (one of which of helychrisum), to be used for improving the resistance to chemotherapeutics in patients under therapy for viral hepatites or tumours, is claimed.

In the WO 03/015522 patent application, the use of an acaricidal composition consisting of a mixture of essential oils (among which the helychrisum) is claimed.

In the FR 2830198 patent, the use of a composition containing helychrisum oil, together with other essential oils for the topical treatment of viral infections, immunodeficiencies and other pathologies, such as the cystic fibrosis, is claimed.

In the FR 2845594 patent, the use of a composition containing helychriSum oil, together with other essential oils for the use in cosmetics or dermatology, is claimed.

In the FR 2774585 patent, the use of a composition containing helychrisum oil, together with other essential oils for stopping the hair loss and fighting for the formation of cuticles (dandruff), is claimed.

In the KR 2003/046949 patent application, the extraction of the oily fraction of *helychrysum angustifolium* and the anti-inflammatory activity of a cosmetic preparation are claimed.

The preparations obtained by the helychrisum drug more generally used at present, are; the decoction, the fluid extract, the syrup, the total dry extract.

By the term "decoction", is understood to mean a liquid which is usually prepared extemporarily at the time of use by placing an opportune drug quantity in cold water, boiling the water and filtering away the coarse residue remained in suspension before consuming the extraction liquid.

By the term "fluid extract" (hereinafter "fluid helychrisum extract") is understood to mean the liquid, more or less thick, which is obtained by macerating the drug with a proper quantity of solvent mixture, normally hydro alcoholic (alcohol at 60-70° or alcohol at 95°) or hydro glyceric, for a time period varying depending on the kind of drug and, subsequently, filtering the macerated matter in order to eliminate the insoluble residue of the drug.

By the term "syrup" is understood to mean a liquid which is obtained by properly diluting the above fluid extract (normally with water) and adding flavours, sugar and excipients of a different nature.

By the term "total dry extract" (hereinafter, "dry helychrisum extract") is understood to mean the solid residual which is obtained by completely removing, by evaporation, the solvent mixture (hydro alcoholic or hydro glyceric) from the above fluid extract, operating at low temperatures. The total dry helychrisum extract can be also prepared in a freeze-dried form (hereinafter, freeze-dried helychrisum extract", or "extracted freeze-dried helychrisum" in the enclosed Figures).

Unfortunately, also the above helychrisum preparations, even if they are known for their good tolerability, are affected by a series of non negligible drawbacks, typical of the phytotherapeutic preparations just described.

For example, the mixture of the extracted active substances (responsible for the pharmacological activity/s ascribed to the drug) can result too much diluted (as in the case of the fluid extract and/or the syrup) or, even not reproducible, nor standardizable as for the dosage (as in case of decoction).

Furthermore, the extraction methods above described are not able to selectively extract only the pharmacologically beneficial active substances, but, at the same time, they extract a significant quantity of substances at least pharmacologically inert, if not potentially or really toxic.

Therefore, for the purpose of the optimization of the pharmacological activity of the helychrisum and the standardization of the doSages, in particular for the treatment of the acute and chronic pathologies, it should be useful to be able to provide pharmaceutical compositions including a therapeutically effective quantity of helychrisum, characterized by a high quantity of pharmacologically beneficial active substances (as a standardized title) and a low quantity of pharmacologically inactive, if not even toxic, substances. Likewise, it should be useful to be able to provide pharmaceutical compositions wherein the quantity of mixture including the beneficial active substances of the helychrisum (dose) is, beside being standardized in the components thereof, substantially lower to the one normally administered with the traditional preparations above described.

SUMMARY OF THE INVENTION

Compositions having the features above described are not known.

Therefore, there remains the need of being able to provide pharmaceutical compositions based on helychrisum extract, including a therapeutically effective quantity of the same, containing the greatest possible quantity of pharmacologically beneficial active substances and the lowest possible quantity of pharmacologically inactive, if not toxic, substances.

An object of the present invention is to give an adequate answer to the need above described.

DETAILED DESCRIPTION OF THE INVENTION

These and other objects, which will result evident from the following detailed description, have been attained by the Applicant, which has unexpectedly found that a water insoluble fraction of the above fluid helychrisum extract is able to solve the problem above described.

By easiness, hereinafter said water insoluble fraction will be shown by the term "water insoluble helychrisum extract" (or "water insoluble helychrisum fraction" in the enclosed Figures).

It is an object of the present invention a water insoluble helychrisum extract, as reported in the appended independent claim.

Another object of the present invention is a process for preparing said water insoluble helychrisum extract, as reported in the appended independent claim.

Another object of the present invention is then a pharmaceutical composition including the above water insoluble helychrisum extract, as reported in the appended independent claim.

Another object of the present invention is the use of said water insoluble helychrisum extract for the preparation of pharmaceutical compositions, as reported in the appended independent claim.

Further objects of the present invention are the use of said extract as a medicament and/or for the preparation of pharmaceutical compositions for the treatment of pathological states in humans and animals, as reported in the appended claims.

Preferred embodiments of the present invention are reported in the appended dependent claims.

The present invention is shown in detail in the following description. Said invention is further illustrated also with the help of the enclosed FIGS. 1 to 3, wherein.

As it has been previously mentioned, the Applicant has unexpectedly found that the therapeutic properties of the *Helichrysum italicum* are substantially referable/ascribable to a water insoluble fraction of the fluid helychrisum extract (that is, that fraction previously defined as "water insoluble helychrisum extract", obtainable from the drug (or from its fluid extract, or from its total dried/freeze-dried extract) by means of a particular and original extraction process.

According to a preferred embodiment of the present invention, the water insoluble helychrisum extract is obtainable by means of an extraction process from the drug including the following steps:

1) extracting the drug with a water/organic solvent mixture in order to give the hydro-organic fluid tract of helychrisum;
2) evaporating the organic solvent from said fluid extract, to give the precipitation of a water insoluble fraction from the remaining aqueous fraction;
3) separating said water insoluble fraction from said aqueous fraction, to give a water insoluble solid extract.

When one wishes to start from the total dried/freeze-dried extract, instead of the drug or the fluid extract, then the steps 1) and 2) should be replaced by the preparation of a suspension of said total dried/freeze-dried extract in a proper quantity of water.

In the step 1), the water/organic solvent mixture has a water content, relative to the total volume of the mixture, from 15% (v/v) to 85% (v/v); preferably, from 20% (v/v) to 65% (v/v); more preferably, approximately equal to 30% (v/v).

The organic solvent employed in said mixture is a partly or completely water soluble solvent, preferably selected from acetone and an alcohol containing from one to three carbon atoms (methanol, ethanol, n-propanol, isopropanol), or their mixtures; more preferably, said organic solvent is ethanol.

In a preferred embodiment of the invention, said water/organic solvent mixture consists of 70° ethanol.

In this case, in particular, the ethanol is produced from biological wheat and consists of 66.12 parts (by weight) of alcohol against 33.88 parts (by weight) of water.

In the step 2), the evaporation of said organic solvent is preferably carried out under a reduced pressure; preferably, at a residual pressure from 600 mbar to 150 mbar.

Preferably, the evaporation is then continued until the initial volume of the fluid extract coming from the passage 1) has been reduced at a value from about ⅓ to about ⅐ of said initial volume; preferably, from about ¼ to about ⅙ of the initial volume; more preferably, at about ⅕ of the initial volume.

In the step 3), the separation of said water insoluble fraction from the aqueous fraction is preferably carried out by centrifugation or filtration; more preferably, by centrifugation.

In a preferred embodiment of the invention, said extraction process further includes the step of:
4) drying the water insoluble extract coming from the above passage 3).

In the step 4), the drying is carried out in such conditions to avoid the degradation of said extract; preferably, said drying is carried out by freeze-drying; preferably, of an aqueous suspension of the extract itself.

The above step 1) (that is the preparation of the hydro-organic fluid extract of helychrisum) has the object of extracting the greater possible number of pharmacologically active substances existing in the drug.

In a preferred embodiment of the invention, said step includes at least one of the following steps (preferably all of them):
1a) extracting (by maceration and percolation) the drug, using a drug/solvent mixture (D/S) weight ratio (w/w) from 1:1 to 1:25; preferably, from 1:5 to 1:20; more preferably, from 1:10 to 1:15; still more preferably, of about 1:13;
1b) extracting the drug at a temperature from 20° C. to the reflux temperature of the organic solvent used, or the water/organic solvent mixture; preferably, at a temperature of 60° C.;
1c) extracting the drug in two steps: namely, by carrying out a first extraction, preferably with about 60% of the solvent mixture, followed by a second extraction, with the remainder about 40%, and joining together the two extracts;
1d) filtering the end fluid extract for the purpose of clarifying the same.

The above step 2) (that is the partial evaporation of the hydro-organic solvent mixture) has the purpose of completely removing the organic solvent from the fluid extract deriving from the step 1) and partly concentrating the water until the water insoluble fraction (namely, the water insoluble helychrisum extract), which contains the mixture of the pharmacologically beneficial active substances of the drug, has precipitated.

In a preferred embodiment of the invention, said step 2) includes at least one of the following steps (preferably all of them):
2a) evaporating the organic solvent under a reduced pressure; preferably at a residual pressure from 600 mbar to 150 mbar;
2b) carrying out said evaporation at a outer temperature from 40° C. to 130° C.; preferably, from 50° C. to 70° C.; more preferably, at about 60° C.

The above step 3) (namely the separation of the water insoluble extract of helychrisum from the aqueous step) has the putpose of isolating and washing the helychrisum extract from the residual aqueous fraction, which includes a series of non pharmacologically active water soluble products.

In a preferred embodiment of the invention, said step 3) includes at least one of the following steps (preferably all of them):
3a) centrifuging the solid/water phase mixture resulting from the passage 2), for example by means of a horizontal centrifuge;
3b) collecting the solid (that is the water insoluble extract of helychrisum);
3c) washing said solid with water; for example, using a solid/water weight ratio (w/w) from 1:1 to 1:10; preferably, from 1:1 to 1:5.

The above additional, possible, passage 4) has the purpose of transforming the isolated and washed water insoluble helychrisum extract in a powder utilizable for preparing and standardizing the desired different pharmaceutical formulations based on helychrisum.

In a preferred embodiment of the invention, said step 4) includes:
4a) suspending the solid helychrisum extract in water;
4b) freezing said suspension;
4c) freeze-drying said frozen suspension;
4d) milling the obtained freeze-dried product for the purpose of rendering homogeneous the particle size of solid freeze-dried helychrisum extract.

The above freeze-drying process is carried out using equipments and working conditions known to a skilled in the art.

The solid helychrisum extract can also be freeze-dried in the presence of proper excipients, such as, for example: stabilizers, preservatives, flavourings, sweeteners.

In an embodiment of the invention, the Italic helychrisum used for the preparation of the pharmacologically active water insoluble extract, has been cultivated in a calcareous and half-arid land typical of the Tuscany-Emilia Apennine. The cultivation, arranged at 600 meters above the sea-level, was exposed to South-South-West, with an optimum exposition to the sun's rays and a slope about 15-200. The harvesting has been carried out in July, at the beginning of the blossom time, cutting the tender tops of the branches for 10 cm about and avoiding the lower wooden portion. The fresh harvest has been immediately dried in air furnaces at a temperature of 40-45° C. The dried drug thus obtained has shown a flavonoid content, expressed as isoquercitrin, from 0.42% to 0.50% by weight, based on the total weight of the drug.

Furthermore, a content in caffeil-quinic derivatives, expressed as chlorogenic acid (monoester of the quinic acid with the caffeic acid), from 2.5% to 3.1% by weight, based on the total weight of the drug, has been determined.

As pointed out in the enclosed FIG. 1 (FIG. 1 —chromatogram a)), the chromatographic profile of the total freeze-dried helychrisum extract, obtained from the drug by the HPLC-MSD method, described hereinafter in the Example 4, is characterized by the presence of a series of signals/products having widely varying retention times (from few minutes to about 40 minutes, until a series of signals having retention times lower than about 60 minutes).

The chromatographic profile of the water soluble fraction of the helychrisum extract (FIG. 1 —chromatogram b)) is, on the contrary, characterized by the presence of the series of signals having retention times lower than about 40 minutes.

In turn, the chromatographic profile of the water insoluble extract of helychrisum (FIG. 1 —chromatogram C)) is, on the contrary, characterized by the presence of the series of signals having retention times higher than about 60 minutes.

Figure 2:
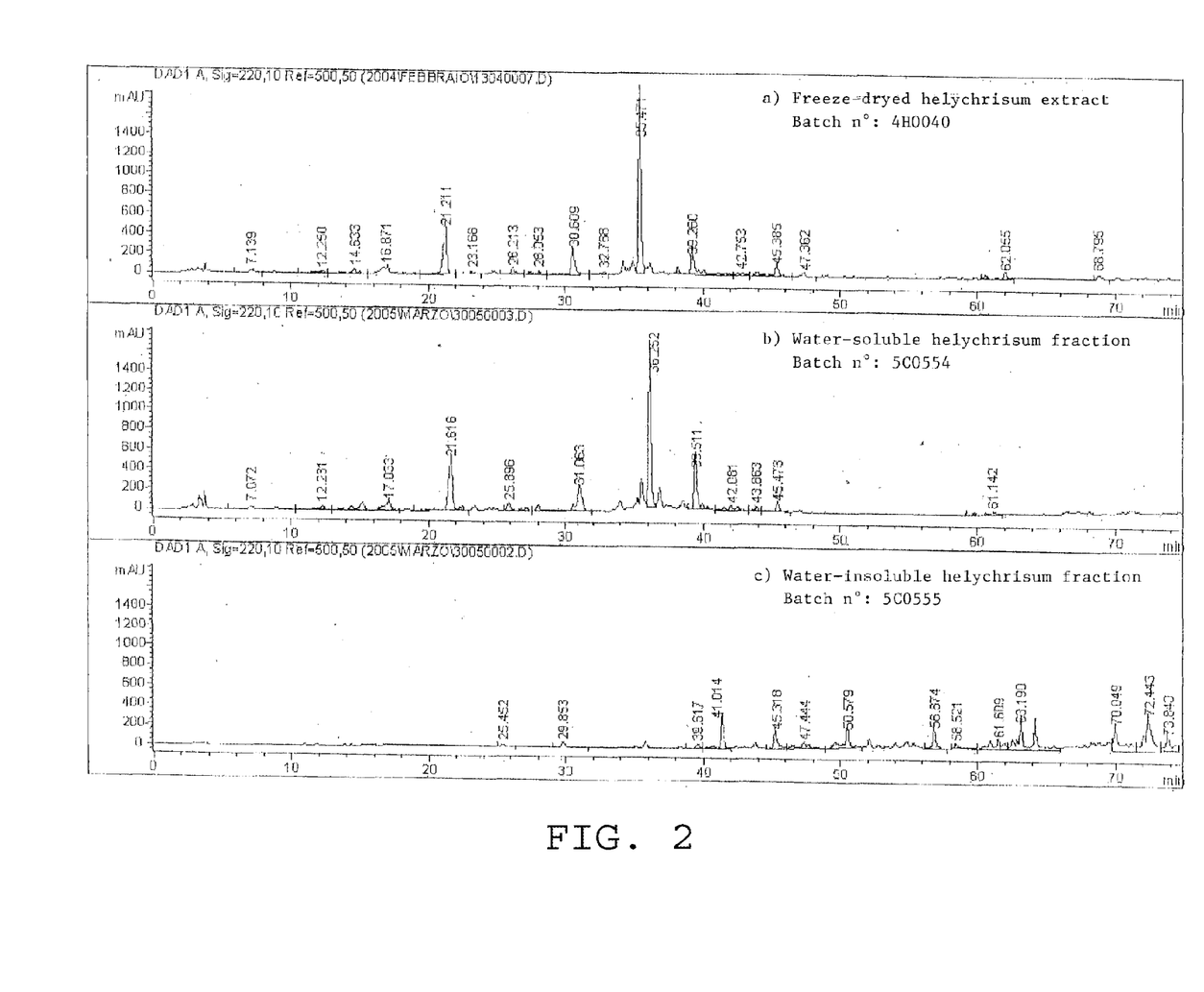
FIG. 2 shows, from the top downwards, the comparison between the chromatographic profiles of, respectively: a) freeze-dried helychrisum extract; b) water soluble helychrisum fraction (namely the fraction of the freeze-dried helychrisum extract soluble in water); c) water insoluble helychrisum fraction (namely the water insoluble helychrisum extract according to the present invention), wherein the chromatograms have been obtained with a detector adjusted to 220 nm, with the HPLC-DAD method described in the following experimental section (Example 4)
Figure 3:
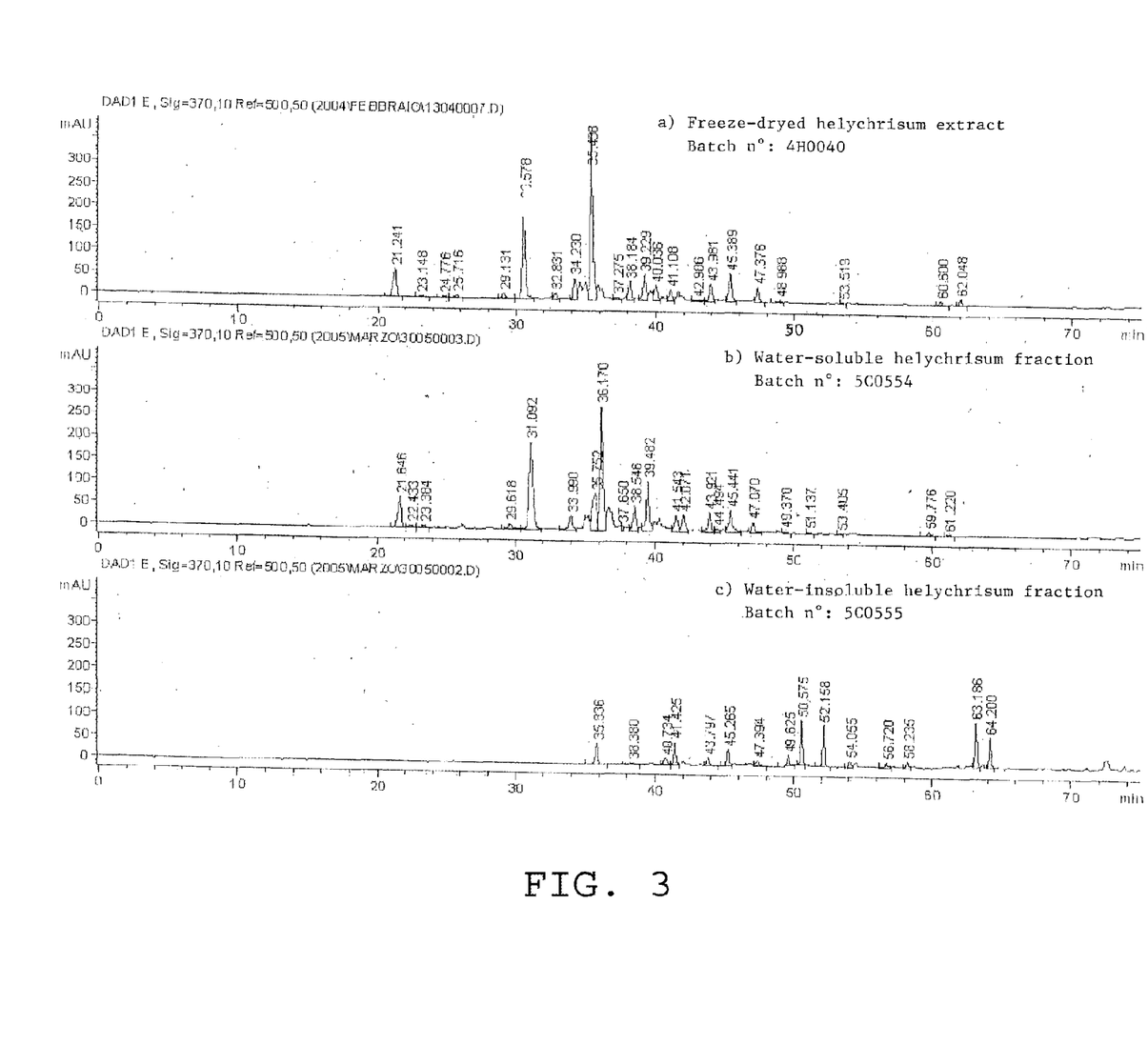
FIG. 3 shows, from the top downwards, the comparison between the chromatographic profiles of, respectively: a) freeze-dried helychrisum extract; b) water soluble helychrisum fraction (namely the fraction of the freeze-dried helychrisum extract soluble in water); c) water insoluble helychrisum fraction (namely the water insoluble helychrisum extract according to the present invention), wherein the chromatograms have been obtained with a detector adjusted to 370 nm, with the HPLC-DAD method described in the following experimental section (Example 4).

The same type of situation is also substantially confirmed by the chromatograms of the enclosed FIGS. 2 and 3, from which it is evident that the (active) substances, forming the water insoluble helychrisum extract are characterized by retention times higher than about 40 minutes (differently from the total freeze-dried total and the water soluble fraction).

The water insoluble helychrisum extract corresponds to about 2.3%-2.5% by weight with respect to the total weight of the dry drug and about 13%-15% by weight with respect to the total weight of the total dry extract of the same.

The water insoluble helychrisum extract is characterized by a water solubility (at a room temperature of 25° C.)<10 mg of extract/10 ml of water; preferably, lower than 8 mg/10 ml; more preferably, lower than 5 mg/10 ml.

The solubility study of said extract in other solvents has allowed to individuate the following solubility profile (expressed as mg of water insoluble extract/ml of solvent):

| | |
|---|---|
| ethanol 95° | about 10 mg/0.2 ml; |
| ethyl acetate | about 10 mg/0.5 ml; |
| ethyl ether | <10 mg/1 ml; |
| chloroform | about 10 mg/0.5 ml; |
| dichloromethane | about 10 mg/1 ml; |
| hexane | <10 mg/2.5 ml; |
| toluene | about 10mg/1 ml; |
| acetone | about 10mg/0.8 ml. |

The water insoluble helychrisum extract, obtained according to the extraction method of the present invention, has been additionally characterized by chemical and biological methods, for the purpose of standardizing the same not only from the constituents point of view but also the pharmacological activity:

As for the qualitative characterization of the extract, chromatographic methods have been developed by means of HPLC/DAD and HPLC/MSD, as described hereinafter in the Example 4, which have allowed to acquire the characteristic chromatographic profile (fingerprint) of the extract itself.

Figure 1:
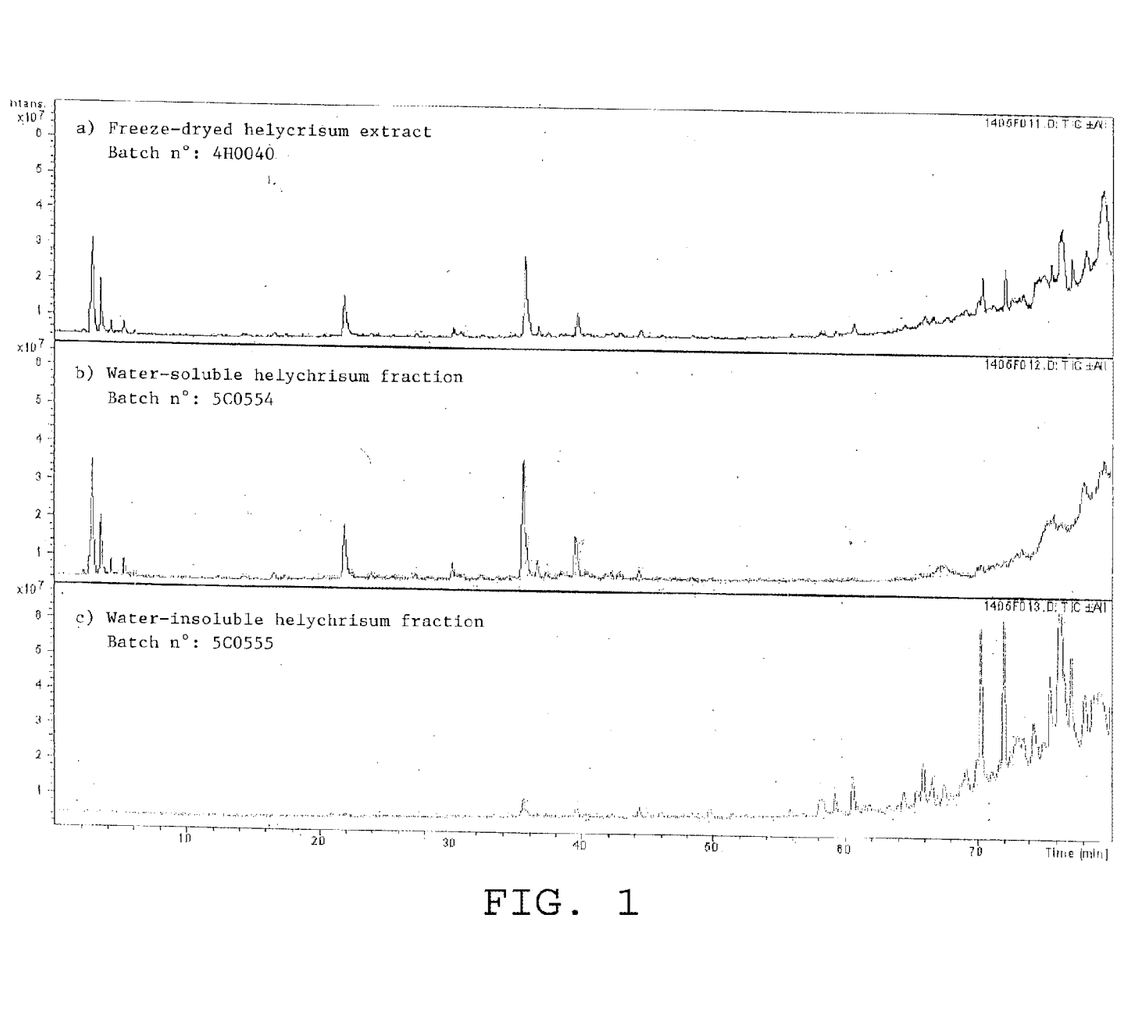
FIG. 1 shows, from the top downwards, the comparison between the chromatographic profiles of, respectively: a) freeze-dried helychrisum extract; b) water soluble helychrisum fraction (namely the fraction of the freeze-dried helychrisum extract soluble in water); c) water insoluble helychrisum fraction (namely the water insoluble helychrisum extract according to the present invention), wherein the chromatograms have been obtained with the HPLC-MSD method described in the following experimental section (Example 4)

As already above reported, the water insoluble helychrisum extract resulted characterized by the chromatographic profiles (fingerprint) c) disclosed in enclosed FIGS. 1-3.

As for the quantitative characterization of said extract; the same has been carried out through the determination of two important classes of constituents, the flavonoids and the caffeic-quinic derivatives.

The spectrophotometric methods employed for carrying out such quantitative determinations are described in detail in the following experimental section (Examples 2 and 3, respectively).

The water insoluble helychrisum extract resulted characterized by a flavonoid content, expressed as isoquercitrin, from 2% to 15% by weight, with respect to the total weight of the extract; preferably, from 2.5% to 10% by weight; more preferably, from about 3% to about 8% by weight.

On average, said flavonoid content is from about 3.5% to 5.5% by weight; preferably, around 4% eight. Therefore, in the water insoluble extract, the flavonoids are resulted more concentrated with respect to their starting concentration in the dry drug.

Furthermore, the water insoluble helychrisum extract is resulted characterized by a content of caffeil-quinic derivatives, expressed as chlorogenic acid, from 0.5% to 5% by weight, with respect to the total weight of the extract; preferably, from 2.86% to 3.5% by weight; more preferably, from 2.9% to 3.4% by weight; on average, of about 3% by weight.

The water insoluble helychrisum extract has also been characterized by determining its protection activity from the proteinic denaturation, expressed as $EC_{50}$.

Said extract has proven to be standardized to inhibit a 50% proteinic denaturation when used at a concentration of 0.2 mg/ml.

The pharmacological activities ascribed to the traditionally used extracts of the helychrisum, have resulted referable/ascribable to the mixture of compounds contained in the water insoluble helychrisum extract obtained through the innovative extraction/separation process of the present invention.

The anti-inflammatory/pain-killing activity of said extract has been documented, at a pre-clinical level, using the in vitro test of the proteinic denaturation and of the Writhing in the mouse.

The anti-allergic/anti-asthmatic activity has further been documented on the bronchospasm and the plasma extravasation induced by ovalbumin in guinea pigs sensitized to this compound.

The studies have confirmed that the pharmacological activity of the water insoluble helychrisum extract, obtained by the extraction/separation process of the present invention, is the one known of the whole drug. Moreover, the pharmacological activity of said extract has resulted greater and better than the one ascribable to the drug, thus allowing to prepare pharmaceutical compositions with a reduced and standardized dosage which allow the repeatability of the dosages and the treatments.

Advantageously, the water insoluble helychrisum extract has shown to possess a good anti-inflammatory activity.

Furthermore, said extract has a good pain-killing activity.

Furthermore, said extract has a good anti-allergic activity.

Therefore, the water insoluble extract of the present invention has proved to be particularly useful for a use as a medicament; in particular for preparing pharmaceutical compositions to be used in a medical field in the therapy of pathologic states in human and animal, as above pointed out.

Therefore, it is also a subject of the present invention a process for the preparation of a pharmaceutical composition containing a therapeutically effective quantity of water insoluble helychrisum extract; said process includes at least a step in which said extract is additioned with opportune pharmacologically acceptable co-formulations.

Said pharmaceutical compositions can be used both for oral and topical administration (including aerosol).

Said pharmaceutical compositions are preferably formulated in admixture with appropriate excipients, such as vehicles, lubricants, dispersants, flavourings, sweeteners, stabilizers, preservatives, antioxidants, additives, such as amino acids, vitamins, enzymes commonly used in the pharmaceutical formulation art.

By mere way of absolutely not limiting example, amongst the particularly preferred excipients and additives there may be mentioned starch, flavours, such as those of mandarin, grapefruit, strawberry, bilberry, all fruits, sucrose, glucose, ascorbic acid, glutamine, arginine, inulin.

Particularly preferred compositions of the present invention are those for oral administration (including the sublingual one).

Typical preferred formulation forms are, for example, capsules, beads, syrups, solutions or suspensions ready-to drink, powders or granulates in sachets (to be suspended or dissolved in water or in non-carbonated and non-alcoholic beverages at the moment of use) or analogous forms, tablets, effervescent formulations:

The compositions of the present invention can also be formulated in a coated, lacquered, encapsulated or microencapsulated form, such that to result gastro-resistant.

Said compositions can also be formulated in a controlled-release form, so as to selectively deliver the active substances in the intestinal tract, in particular within the colon.

Other preferred compositions of the invention are those for topical administration.

Said compositions can be prepared in form of pomades, ointments, gels; or they can be opportunely formulated and incorporated in transdermal vehicles, such as for example plasters.

The compositions of the present invention are prepared in a traditional way by using, depending on the kind of formulation that one wishes to carry out, preparative techniques known to the pharmaceutical artisan skilled in the art.

The compositions of the present invention have proved to be particularly useful for the prevention and/or the treatment of different pathologies, both for topical use (for example for the treatment of eczema and atopic dermatitis, irritative contact dermatitis, allergic contact dermatitis), and for systemic use (for example chronic rheumatic affections, inflammatory pathologies, acute pain from fractures consequences, asthma and allergic rhinitis).

The present invention is described hereinafter, by mere way of non limiting example, by means of some experimental examples.

EXAMPLE 1

Preparation of the water insoluble extract of italic helychrisum, starting from the drug.

178 kg of dry drug of helychrisum were extracted with 70° ethanol with the D/S weight ratio 1:13. A first extraction with the 60% of the solvent mixture was carried out over 5 h at 60° C., then the hydro alcoholic extract was removed and the drug extracted a second time with the remaining 40% of the solvent mixture for 3 h at 60° C. The extraction was carried out by percolation/maceration.

The pooled hydro alcoholic extracts were filtered (weight of the fluid extract=1830 kg) and concentrated under vacuum (60° C., 600 mbar) until 380 kg of a concentrated aqueous suspension were obtained.

The concentrated aqueous suspension was subjected to centrifugation through a horizontal centrifuge. In this way, the precipitate was separated from the remaining water phase in form of a black-coloured thick, solid mass.

6 kg of wet solid precipitate and 370 kg of water phase were thus obtained.

The wet precipitate obtained was washed with 6 l of ultra-neat water, then subjected to freeze-drying giving 4.2 kg of water insoluble helychrisum extract, equal to about 2.4% by weight, based on the initial weight of the drug employed.

The water phase was, in turn, subjected to freeze-drying giving 26 kg of a water soluble residue, or fraction, equal to about 14.6% by weight, based on the initial weight of the drug employed.

The freeze-dried water insoluble extract was milled by a cryo-mill to give 3 kg of a powder which was stored at a temperature of +4° C., in a sealed and under vacuum aluminium sachet. The freeze-dried water insoluble extract resulted characterized by a content of flavonoids, expressed as isoquercitrin, equal to 3.78% by weight, based on the total weight of the extract, and a content of caffeic-quinic derivatives, expressed as chlorogenic acid, equal to 3.36% by weight, based on the total weight of the extract.

The chromatographic profiles of the water insoluble extract thus obtained are those respectively reported in the chromatograms c) of the enclosed TAB. 1-3.

EXAMPLE 2

Spectrophotometric method for the determination of the flavonoid content (expressed as isoquercitrin) in the drug and the water insoluble helychrisum extract (modification of the method described in Eur. Ph, v Ed., monograph of Sambuci flos)

About 0.60 g of pulverized drug (or about 0.30 g of water insoluble helychrisum extract) were treated with 1 ml of aqueous solution (5 g/l) of hexamethyltetramine, additioned with 20 ml of acetone and 2 ml of a hydrochloric acid solution (70 g of conc. hydrochloric acid in 100 ml of water); the suspension was heated until boiling for 30 minutes.

A filtration through cotton in a 100 ml volumetric flask is carried out. The residue and the cotton were treated in two stages each time with 20 ml of refluxed acetone over 10 minutes; the two washes were added to the parent solution and, after cooling, adjusted to volume (100 ml) with acetone (Solution A).

20 ml of the solution A (10 ml in case of the water insoluble extract) were added to 20 ml of water and extracted with ethyl acetate (1×15 ml, 3×10 ml).

The pooled extract were washed with water (2×50 ml), dried over dry sodium sulphate and adjusted to volume with ethyl acetate in a 50 ml volumetric flask (Solution B).

10 ml of the solution B were transferred in a 25 ml flask and added with 1 ml of aluminium trichloride solution (at 20 in methyl alcohol containing 5% of glacial acetic acid) and adjusted to volume with the methanol solution (50 ml/l) of glacial acetic acid. (Solution under examination). 10 ml of the solution B were transferred in a 25 ml flask and adjusted to volume with the methanol solution (50 ml/l) of glacial acetic acid. (Comparison solution).

After 30 minutes, the absorbance of the solution under examination was measured, at 425 nm, with respect to the comparison solution.

Knowing that $A_{1\%, 1cm}$ of the isoquercitrin is equal to 500 at 425 nm, the percent content of flavonoids, expressed as isoquercitrin, was computed with the formula:

$$\% = (A \times V \times F)/A_{1\%, 1cm} \times p$$

wherein:
p=weight of the sample expressed in grams
A=absorbance of the sample at 425 nm
V=extraction volume (100 ml)
F=dilution factor (6.25)

EXAMPLE 3

Spectrophotometric method for the determination of the caffeil-quinic acids content (expressed as chlorogenic acid) in the drug and the water insoluble helychrisum extract (isolation of the orthodiphenolic fraction in form of lead salt) (modification of the method described in FU IX ed, monograph of the Cynara dry extract).

About 0.50 g of pulverized drug (or 0.30 g in case of the water insoluble helychrisum extract) were treated with 40 ml of water until boiling. The suspension was heated until boiling, filtered through cotton in a centrifuge tube. To the still hot solution, 2 ml of a solution saturated with lead (PbII) acetate were added. Cooling and centrifugation were performed, and the clear supernatant solution was eliminated. The precipitate was washed with water (5 ml), then again centrifuged removing the water phase. The precipitate was dissolved in 70 ml of a 10% acetic acid aqueous solution and heated to ebullition. The hot mixture was filtered through cotton, 2 ml of 20% sulphuric acid were added. The lead sulphate precipitate was separated by centrifugation, the clear solution was transferred in a 100 ml volumetric flask. The precipitate remained on the bottom of the centrifuge tube was washed with 5 ml of 10% acetic acid; the washing solution, after centrifugation, was transferred in the same flask, where it was adjusted to an end volume of 100 ml with 10% acetic acid.

1 ml of this solution was diluted to 25 ml with methanol: the absorbance of the solution at 325 nm was read, against a solution obtained by diluting 1 ml of 10% acetic acid to 25 ml with methanol.

Knowing that $A_{1\%, 1cm}$ of the chlorogenic acid at 325 nm is equal to 485, the percent content of caffeic-quinic acids, expressed as chlorogenic acid, was computed with the formula:

$$\% = (A \times V \times F)/A_{1\%, 1cm} \times p$$

wherein:
A=absorbance of the sample at 425 nm.
F=dilution factor (25)
p=weight of the sample expressed in grams
V=extraction volume (100 ml)

EXAMPLE 4

HPLC/DAD and HPLC/MSD methods for the acquisition of chromatographic profile of the helychrisum extracts (applicable, respectively, over: drug, freeze-dried extract, water insoluble extract and water soluble fraction)

The study of the HPLC chromatographic profiles was carried out by acquiring the chromatograms by means of two different detectors (DAD: Photo Diode Array; MSD: Ion Trap, Agilent, mod SL) with different analytical methodologies in the two cases.

HPLC/DAD Method

Equipment:
HPLC Agilent series 1100, fitted with vacuum degasser, quaternary pump, self-sampler, thermostated compartment at 20° C. for the housing of two columns, diode array detector (DAD).

Reverse phase analytical column Prodigy RP-18 (250 mm×4.6 mm, 100 Å, 5μ, Phenomenex, USA) with a pre-column RP-18 (4 mm×3 mm).

Preparation of the Solutions to be Examined:
  drug: extracting 0.5 g of dry drug with two subsequent portions of 25 ml of 50° ethanol, over 30' in an ultrasonic bath; centrifugation is carried out, the extracts are pooled and adjusted to volume to 50 ml in a volumetric flask;
  freeze-dried extract: extracting 0.1 g of extract with 10 ml of 50° ethanol, over 30' in an ultrasonic bath; centrifugation is carried out and the overlying solution is examined, as described in the Process;
  water insoluble extract (or water insoluble fraction): extracting 0.1 g with 10 ml of 50° ethanol, over 30' in an ultrasonic bath, centrifugation is carried out and the overlying solution is examined, as described in the Process.
  water soluble fraction: extracting 0.1 g with 10 ml of 50° ethanol, over 30' in an ultrasonic bath, centrifugation is carried out and the overlying solution is examined, as described in the Process.

Process:
  collecting 0.5 ml of the solution to be examined, filtering over a cellulose acetate filter (0.45 μm), injecting 20 μl in the apparatus.
  Flow rate: 1 ml/min
  Elution solvent: 0.2% $H_3PO_4$ in water/methyl alcohol, in a gradient (Table no. 1)

TABLE no. 1

| minutes | Gradient composition: | |
|---|---|---|
| | 0.2% $H_3PO_4$ in water | $CH_3OH$ |
| 0 | 90% | 10% |
| 35 | 50% | 50% |
| 75 | 5% | 95% |

The chromatograms are acquired at 220, 265, 280 330 and 370 nm.

HPLC/MSD Method

Equipment:
HPLC Agilent series 1100, fitted with vacuum degasser, binary pump, self-sampler thermostated at 10° C., compartment thermostated at 20° C. for the housing of two columns, diode array detector (DAD) and ion trap mass detector, model SL.

Reverse phase analytical column Prodigy RP-18 (250 mm×4.6 mm, 100 Å, 5μ, Phenomenex, USA) with a pre-column RP-18 (4 mm×3 mm).

Preparation of the Solutions to be Examined:
  drug: extracting 0.5 g of dry drug with two subsequent portions of 25 ml of 60% methanol, over 30' in an ultrasonic bath; centrifugation is carried out, the extracts are pooled and adjusted to volume at 50 ml in a volumetric flask, always with 605 methanol;
  freeze-dried extract: dissolving 10 mg in 10 ml of 60% methanol over 30' in an ultrasonic bath;
  water insoluble extract (or water insoluble fraction): dissolving 10 mg in 10 ml of methanol, over 30' in an ultrasonic bath;
  water soluble fraction: dissolving 10 mg in 10 ml of 0.60% methanol over 30' in an ultrasonic bath.

Process:
  collecting 0.5 ml of the solution to be examined, filtering over a cellulose acetate filter (0.45 μm), injecting 5 μl in the apparatus.
  Flow rate: 1 ml/min
  Elution solvent: 0.025% formic acid in water/methyl alcohol, in a gradient (Table no. 2)

TABLE no. 2

| minutes | Gradient composition: | |
|---|---|---|
| | 0.025% $HCO_2H$ in water | $CH_3OH$ |
| 0 | 90% | 10% |
| 35 | 50% | 50% |
| 75 | 5% | 95% |
| 80 | 5% | 95% |

Before the introduction within the mass detector, the flow is properly split to 0.6 ml/min. through a T-valve using, for the different connections, capillary tubes with a same caliper but different length. The analyses have been carried out using the ESI source and selecting negative ions. In Table no. 3, the parameters for the acquisition of the mass spectra during the chromatographic elution are reported.

TABLE no. 3

| Acquisition modes of the mass spectra | | | | | |
|---|---|---|---|---|---|
| Source | ESI | Nebulizer | 50 | Capillary | 3500 |
| Polarity | Negative | Dry gas | 10 | Skimmer | −40.0 |
| Target | 30000 | Dry Temp. | 350 | Cap. exit | −90.8 |
| MAT | 100 | Oct. RF | 108.9 | Oct 1DC | −12.00 |
| Scan | 100/1500 | Lens 1 | 5.0 | Oct 2DC | −1.70 |
| Average | 7 (RA = 2) | Lens 2 | 60.0 | Trap drive | 55.00 |

For the water insoluble extract, a specific HPLC/MSD method was further developed, capable of pointing out with a greater accuracy the characteristic components. The methodology is differentiated from the preceding one only for the used gradient, whose composition is reported in the Table no. 4.

TABLE no. 4

| | Gradient composition | |
|---|---|---|
| minutes | 0.025% HCO$_2$H in water | CH$_3$OH |
| 0 | 30% | 70% |
| 75 | 5% | 95% |
| 80 | 5% | 95% |

Control of the Anti-Denaturant Activity

The test is carried out in vitro, using electrophoresis techniques, and allows to correlate the anti-denaturant activity exerted by the water insoluble helychrisum extract on plasma proteins and expressed as EC$_{50}$, to the anti-inflammatory activity of vegetal extracts. In the same test, in fact, the FANS are capable of inhibiting the denaturation of the proteins.

The invention claimed is:

1. A process for preparing a water insoluble *Helichrysum italicum* extract, comprising:
   1) extracting *Helichrysum italicum* with a water/organic solvent mixture in order to yield a hydro-organic fluid *Helichrysum italicum* extract which contains a water soluble *Helichrysum italicum* extract and a water insoluble Helichrysum italicum extract;
   2) evaporating the organic solvent from said hydro-organic fluid Helichrysum italicum extract, to yield a remaining aqueous fraction containing the water soluble *Helichrysum italicum* extract and the water insoluble *Helichrysum italicum* extract; and
   3) separating by centrifugation or by filtration the water insoluble *Helichrysum italicum* extract from the remaining aqueous fraction to yield a water insoluble solid *Helichrysum italicum* extract.

2. Process according to claim 1, wherein, in step 1), said water/organic solvent mixture has a water content, based on the total weight of the mixture, from 15% (v/v) to 85% (v/v).

3. Process according to claim 1, wherein, in step 1), said organic solvent is selected from the group consisting of acetone, an alcohol containing one to three carbon atoms, and mixtures thereof.

4. Process according to claim 3, wherein said alcohol is selected from the group consisting of methanol, ethanol, n-propanol, and isopropanol.

5. Process according to claim 1, wherein, in step 2), said evaporation of the organic solvent is carried out under a reduced pressure.

6. Process according to claim 5, wherein said evaporation in step 2 is continued until the volume of the fluid extract has been reduced to a value of about ⅓ to about ⅐ of the volume of the fluid extract coming from step 1.

7. Process according to claim 1, further including the step of: drying said water insoluble solid *Helichrysum italicum* extract yielded by step 3).

8. Process according to claim 7, wherein said drying step is carried out in such conditions to avoid extract degradation.

9. Process according to claim 1, wherein, in the step 1), said water/organic solvent mixture has a water content, based on the total weight of the mixture, from 20% (v/v) to 65%(v/v).

10. Process according to claim 1, wherein, in step 1), said water/organic solvent mixture has a water content, based on the total weight of the mixture, approximately equal to 30% (v/v).

11. Process according to claim 4, wherein, in step 1), said water/organic solvent mixture has a water content approximately equal to 30% (v/v) and an ethanol content of 70% (v/v), based on the total weight of the mixture.

12. Process according to claim 3, wherein said alcohol is ethanol.

13. Process according to claim 1, wherein, in step 2), said evaporation of the organic solvent is carried out at a residual pressure from 600 mbar to 150 mbar.

14. Process according to claim 5, wherein said evaporation in step 2 is continued until the volume of the fluid extract has been reduced to a value of about ¼ to about ⅙ of the volume of the fluid extract coming from step 1.

15. Process according to claim 5, wherein said evaporation in step 2 is continued until the volume of the fluid extract has been reduced to a value of about ⅕ of the volume of the fluid extract coming from step 1.

16. Process according to claim 7, wherein said drying step is carried out by freeze-drying.

* * * * *